(12) United States Patent
Bathen et al.

(10) Patent No.: US 7,621,743 B2
(45) Date of Patent: Nov. 24, 2009

(54) ORTHODONTIC BRACKET

(75) Inventors: Juergen Bathen, McMinnville, OR (US); Luis Carriere Lluch, Barcelona (ES)

(73) Assignee: Orthodontic Research and Development, S.L., Barcelona (ES)

( * ) Notice: Subject to any disclaimer, the term of this patent is extended or adjusted under 35 U.S.C. 154(b) by 667 days.

(21) Appl. No.: 11/134,189

(22) Filed: May 19, 2005

(65) Prior Publication Data

US 2005/0239012 A1    Oct. 27, 2005

Related U.S. Application Data

(63) Continuation-in-part of application No. 10/535,614, filed as application No. PCT/ES03/00594 on Nov. 25, 2003.

(30) Foreign Application Priority Data

Nov. 26, 2002    (ES)    ................. 200202713

(51) Int. Cl.
*A61C 3/00*    (2006.01)
*A61C 5/08*    (2006.01)
(52) U.S. Cl. ................. 433/10; 433/9; 433/11
(58) Field of Classification Search ............. 433/8–13; 24/132 R, 129 R, 311, 191
See application file for complete search history.

(56) References Cited

U.S. PATENT DOCUMENTS

| 2,011,575 | A |   | 8/1935  | Ford |
| 2,549,528 | A | * | 4/1951  | Russell ................. 433/13 |
| 3,087,244 | A | * | 4/1963  | Huettner et al. ............... 433/14 |
| 3,464,113 | A | * | 9/1969  | Silverman et al. ............. 433/11 |
| 3,578,744 | A |   | 5/1971  | Wildman |
| 3,946,488 | A | * | 3/1976  | Miller et al. .................. 433/11 |
| 4,077,126 | A |   | 3/1978  | Pletcher |
| 4,103,423 | A |   | 8/1978  | Kessel |
| 4,268,249 | A |   | 5/1981  | Forster |
| 4,371,337 | A |   | 2/1983  | Pletcher |
| 4,419,078 | A |   | 12/1983 | Pletcher |
| 4,491,825 | A |   | 1/1985  | Lerner |
| 4,496,318 | A | * | 1/1985  | Connelly, Jr. ................ 433/14 |
| 4,559,012 | A |   | 12/1985 | Pletcher |

(Continued)

FOREIGN PATENT DOCUMENTS

AU    2003282122    6/2004

(Continued)

*Primary Examiner*—Ralph A Lewis
*Assistant Examiner*—Yogesh Patel
(74) *Attorney, Agent, or Firm*—Alix, Yale & Ristas, LLP

(57) ABSTRACT

The present invention provides an improved self-ligating orthodontic bracket. According to one embodiment, the improved orthodontic bracket includes a mounting base for attachment to a tooth surface, an archwire slot formed upon the base and sized for receiving an orthodontic archwire, a channel formed upon the base and transversely oriented to the archwire slot, and a ligating slide member slideably retained within the channel and closeable over the archwire slot for retaining the orthodontic archwire therein, and wherein the ligating slide member includes at least one coplanar resilient retention mechanism for exerting retention forces coplanar with the ligating slide member for holding the ligating slide member in a closed position. In one embodiment, the improved orthodontic bracket comprises a bracket with a ligating slide member slideably retained within a dovetail shaped channel.

62 Claims, 11 Drawing Sheets

U.S. PATENT DOCUMENTS

| | | | |
|---|---|---|---|
| 4,634,662 A | 1/1987 | Rosenberg | |
| 4,655,708 A | 4/1987 | Fujita | |
| 4,698,017 A | 10/1987 | Hanson | |
| 4,712,999 A | 12/1987 | Rosenberg | |
| 5,037,297 A | 8/1991 | Lerner | |
| 5,094,614 A | 3/1992 | Wildman | |
| 5,123,838 A | 6/1992 | Cannon | |
| 5,248,257 A | 9/1993 | Cannon | |
| 5,275,557 A | 1/1994 | Damon | |
| 5,299,934 A | 4/1994 | Suyama | |
| 5,322,435 A * | 6/1994 | Pletcher | 433/11 |
| 5,429,500 A | 7/1995 | Damon | |
| 5,439,378 A | 8/1995 | Damon | |
| 5,466,151 A | 11/1995 | Damon | |
| 5,474,446 A | 12/1995 | Wildman et al. | |
| 5,613,850 A | 3/1997 | Wildman et al. | |
| 5,630,715 A | 5/1997 | Voudouris | |
| 5,782,631 A | 7/1998 | Kesling et al. | |
| 6,042,373 A * | 3/2000 | Hermann | 433/13 |
| 6,053,729 A * | 4/2000 | Brehm et al. | 433/9 |
| 6,071,118 A | 6/2000 | Damon | |
| 6,071,119 A | 6/2000 | Christoff et al. | |
| 6,190,166 B1 | 2/2001 | Sasakura | |
| 6,193,508 B1 | 2/2001 | Georgakis | |
| 6,220,857 B1 * | 4/2001 | Abels | 433/8 |
| 6,247,923 B1 | 6/2001 | Vashi | |
| 6,347,939 B2 | 2/2002 | Abels | |
| 6,357,194 B1 * | 3/2002 | Jones, Jr. | 52/590.1 |
| 6,726,474 B2 | 4/2004 | Spencer | |
| 6,776,613 B2 | 8/2004 | Orikasa | |
| 6,823,638 B2 * | 11/2004 | Stanchfield | 52/588.1 |
| 6,866,505 B2 | 3/2005 | Senini | |
| 7,025,591 B1 * | 4/2006 | Kesling | 433/10 |
| 2002/0025500 A1 * | 2/2002 | Abels et al. | 433/11 |
| 2004/0072117 A1 * | 4/2004 | Farzin-Nia et al. | 433/10 |
| 2004/0157186 A1 | 8/2004 | Abels et al. | |
| 2004/0166458 A1 | 8/2004 | Opin et al. | |
| 2005/0069833 A1 * | 3/2005 | Chikami | 433/9 |
| 2005/0186525 A1 | 8/2005 | Abels et al. | |
| 2005/0239012 A1 | 10/2005 | Bathen et al. | |
| 2005/0244773 A1 | 11/2005 | Abels et al. | |
| 2005/0244774 A1 | 11/2005 | Abels et al. | |
| 2005/0255422 A1 * | 11/2005 | Cordato | 433/10 |
| 2006/0003281 A1 | 1/2006 | Nicholson | |
| 2006/0003282 A1 | 1/2006 | Nicholson | |
| 2006/0024634 A1 | 2/2006 | Lai et al. | |
| 2006/0024635 A1 | 2/2006 | Lai | |
| 2006/0051721 A1 | 3/2006 | Carriere Lluch | |
| 2006/0084025 A1 | 4/2006 | Abels et al. | |
| 2006/0110699 A1 | 5/2006 | Forster | |
| 2006/0147868 A1 | 7/2006 | Lai et al. | |
| 2006/0154196 A1 | 7/2006 | Oda | |

FOREIGN PATENT DOCUMENTS

| | | | |
|---|---|---|---|
| MX | PA/A/2000/0008056 | | 12/2001 |
| WO | WO 99/40871 | | 8/1999 |
| WO | WO0033760 | * | 6/2000 |
| WO | WO 2004/047665 A | | 6/2004 |

* cited by examiner

ORTHODONTIC BRACKET

CROSS-REFERENCE TO RELATED APPLICATIONS

This application is a continuation-in-part of U.S. patent application Ser. No. 10/535,614, filed on May 19, 2005, which is a National Stage of International application Ser. No. PCT/ES2003/000594, filed Nov. 25, 2003, which claims the benefit of Spanish Patent Application No. 200202713, filed Nov. 26, 2002. The specifications of the above applications are incorporated herein by reference.

BACKGROUND OF THE INVENTION

This disclosure relates to improved self-locking or ligatureless orthodontic brackets.

Orthodontic treatment generally comprises dental work to correct irregularities of the teeth or of the relation of the teeth to surrounding anatomy. The irregularities may involve malocclusions with varying degrees of severity. Class 1 malocclusions, for example, may involve spacing irregularities such as excessive crowding or diastema (a gap between two adjacent teeth). Class 2 malocclusions may involve overbite conditions where the upper anterior teeth project labially over the lower anterior teeth. Class 3 malocclusions, in contrast, may involve underbite conditions where the upper anterior teeth close within the lingual side of the lower anterior teeth. For these and other observed irregularities treatment typically involves installation of braces or mechanical aids for repositioning the teeth into correct orthodontic alignment.

Braces generally include orthodontic brackets configured for attachment to the labial or lingual surfaces of the teeth or for attachment to metallic bands secured around the teeth. The brackets typically include archwire slots within which a flexible yet resilient archwire may be engaged. Each bracket is typically bonded to the tooth surface so that the bracket's archwire slot is oriented for engagement with the archwire. Various techniques are used for orienting the brackets. For example, an edgewise appliance comprises braces whereby each bracket is oriented and bonded to the tooth so that the archwire slot is perpendicular to the long axis of the root of the tooth. Alternatively, a straight-wire appliance includes braces whereby each bracket is oriented and bonded to the tooth so that the archwire slot is parallel to the occlusal plane (the biting surfaces of the teeth).

The archwire is typically a curved metallic wire having a rectangular or circular cross section that is bent or twisted prior to engagement with the brackets. The memory or restoring force exerted by the archwire upon the brackets serves to move the teeth into the desired alignment. Throughout the duration of orthodontic treatment the orthodontist periodically adjusts the shape of the archwire (as well as the configuration of other attachments such as elastic bands and so forth) to achieve the correct orthodontic alignment.

Most brackets in current use incorporate tie wings or extensions that project upwardly and downwardly in a gingival-occlusal orientation and require the use of ligatures or ligating modules to hold the archwire within the archwire slots. The ligatures or ligating modules are typically donut-shaped elastomeric rings or wires that are stretched around or twisted around the tie wings.

The use of such ligatures or ligating modules presents a number of inherent disadvantages, some of which are mentioned herein. The small size of the ligatures or ligating modules requires substantial time for installation of the archwire. Because the orthodontist will typically make numerous adjustments to the archwire throughout orthodontic treatment, the orthodontist will likely remove and replace the ligatures or ligating modules numerous times. Hygiene is another problem since the use of ligatures or ligating modules increases the areas where food particles may be trapped. Further, with movement due to chewing or other activities, the ligatures or ligating modules may become detached altogether, allowing the archwire to disengage from the archwire slots.

Ligatures or ligating modules also present other limitations in terms of the forces exerted upon the brackets. For example, the labial or outward force that may be applied to a tooth having a bracket bonded to its labial surface is limited to the strength of the ligature or ligating module in the labial direction. On the same tooth, the force that may be applied in the lingual direction is not so constrained (because the force is applied against the bracket structure rather than the ligature or ligation module). Similarly, the longitudinal (or mesial-distal) forces which may be applied along the direction of the archwire may be limited or defined by the friction between the ligature or ligation module and the archwire. By contrast, a means for locking the archwire within the archwire slot would enhance the forces that may be exerted along the direction of the archwire. Likewise, a means for slideably retaining the archwire within the archwire slot would allow greater flexibility than available from brackets requiring the use of ligatures or ligation modules.

Several self-locking or self-ligating (ligatureless) orthodontic brackets have been designed. However, most of those have complex designs, incorporating features requiring prohibitively expensive machining operations or comprising multiple separate parts, which in turn increases the number of failure modes for such brackets. Other designs have been rejected in the marketplace due to poor quality or poor design, a lack of available features, difficulty of use, or other factors.

What is needed, therefore, is an improved orthodontic bracket that incorporates a self-ligating capability and that offers a different style of bracket than those available today.

The foregoing and other objectives, features, and advantages of the invention will be more readily understood upon consideration of the following detailed description of the invention taken in conjunction with the accompanying drawings.

BRIEF DESCRIPTION OF THE SEVERAL DRAWINGS

For a more complete understanding of the present invention, the drawings herein illustrate examples of the invention. The drawings, however, do not limit the scope of the invention. Similar references in the drawings indicate similar elements.

DETAILED DESCRIPTION OF PREFERRED EMBODIMENTS

In the following detailed description, numerous specific details are set forth in order to provide a thorough understanding of the present invention. However, those skilled in the art will understand that the present invention may be practiced without these specific details, that the present invention is not limited to the depicted embodiments, and that the present invention may be practiced in a variety of alternate embodiments. In other instances, well known methods, procedures, components, and systems have not been described in detail.

Various operations will be described as multiple discrete steps performed in turn in a manner that is helpful for understanding the present invention. However, the order of description should not be construed as to imply that these operations are necessarily performed in the order they are presented, nor even order dependent.

Figure 1:
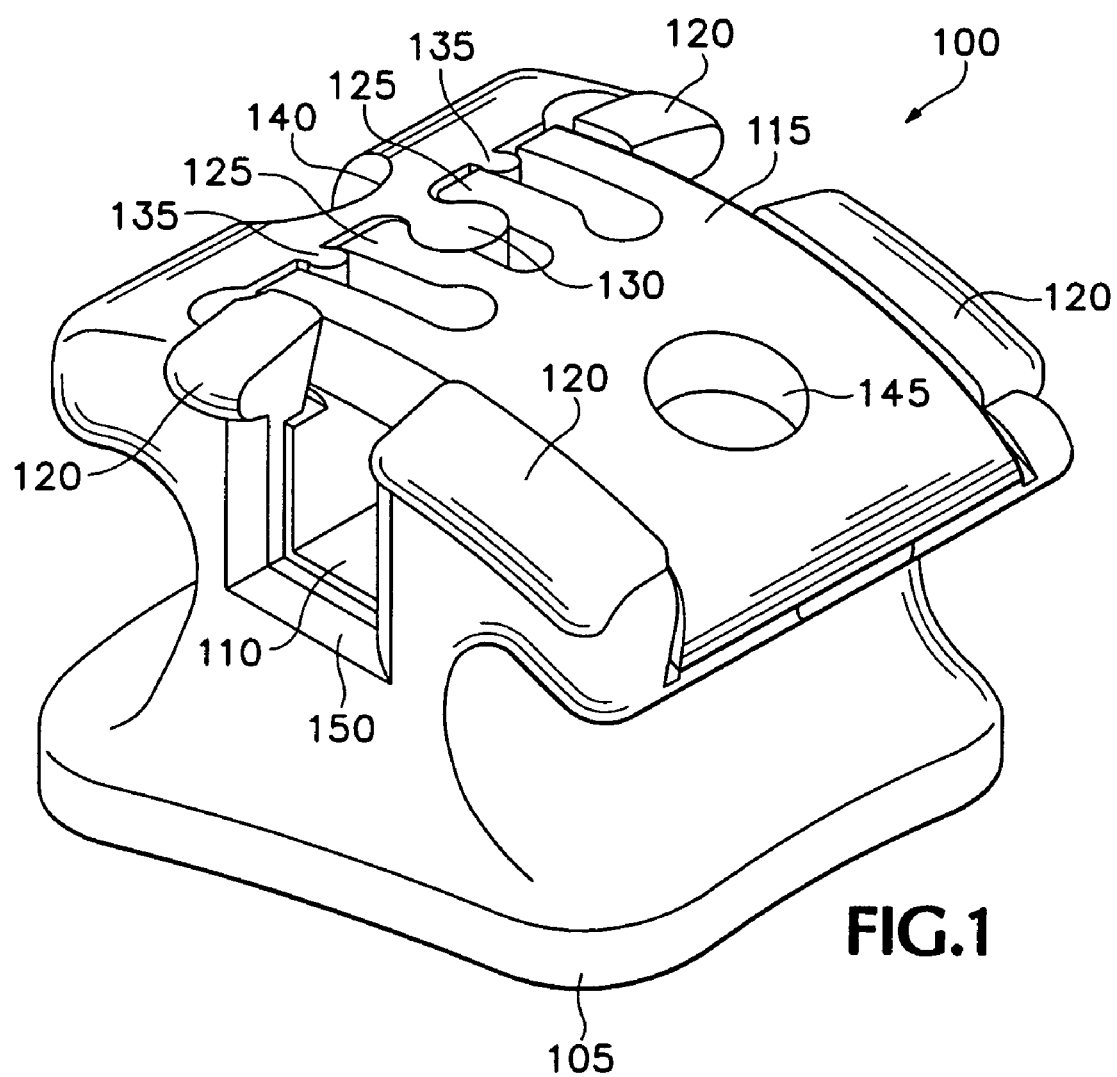
FIG. 1 illustrates an isometric view of an improved orthodontic bracket according to one embodiment of the invention.

Turning now to the several drawings, FIG. 1 illustrates an isometric view of a self-ligating orthodontic bracket 100 according to one embodiment of the invention. The self-ligating orthodontic bracket 100 includes a mounting base 105 for attachment to a tooth surface, an archwire slot 110 formed upon the mounting base 105 and sized for receiving an orthodontic archwire (not shown), and a ligating slide member 115 (shown in a closed position) for retaining an orthodontic archwire within the archwire slot 110. As will be discussed in greater detail below, the ligating slide member 115 may slide within a channel formed between sides 120 and oriented transverse to the archwire slot 110. The ligating slide member 115 preferably includes one or more coplanar resilient retention features (or mechanism) 125 for holding the ligating slide member 115 in a closed position thereby retaining an orthodontic archwire within the archwire slot 110.

As shown in FIG. 1, the one or more coplanar resilient retention features 125 may comprise resilient portions of the ligating slide member 115 suitably formed to allow coplanar deflection and subsequent locking with one or more mating protrusions 130 and 135. Here, the resilient retention features 125 have been designed to deflect outward, perpendicular to the channel formed by sides 120, for lockable engagement with a larger (mating) protrusion 130 and smaller (secondary) protrusions 135. In this configuration, the resilient retention features 125 deflect and engage with the mating protrusions 130 and 135 transverse to and coplanar with the channel formed between sides 120. Consequently, forces exerted normal to the ligating slide member 115, as may arise due to movement of an archwire retained within the archwire slot 110, are not likely to affect the retention of the archwire within the archwire slot 110. Thus, the self-ligating orthodontic bracket 100 more securely retains an archwire than other bracket designs.

Also shown in FIG. 1, the bracket 100 may include orthodontic tool features such as the recess 140 on the top area of the bracket and the recess 145 on the ligating slide member 115. Such features may improve the ease of use of the bracket 100. For instance, an orthodontic tool such as an explorer or scaler may be used with the recess 145 to open or close the ligating slide member 115 to expose or cover the archwire slot 110. Likewise, pliers or another orthodontic tool may be used with the recesses 140 and 145 to close the ligating slide member 115. Further, the recesses 140 and 145, in combination with the protrusion 130 and other visual aspects of the bracket 100, provide a centerline for the bracket 100 useful to aid the orthodontist in the placement of the bracket 100 upon the patient's tooth.

The bracket 100 preferably includes rounded edges, chamfered archwire slot ends 150, and an overall convex shape to improve comfort for the patient wearing the orthodontic appliance. As shown and as will be depicted in many of the illustrations herein, the ligating slide member 115, the channel formed by sides 120, and other features which may define the outer surfaces of the bracket 100 opposite the mounting base 105, preferably follow a convex shape to improve patient comfort and minimize the overall side profile or outward dimension of the bracket 100 from the bonding surface of the mounting base 105.

Figure 2:
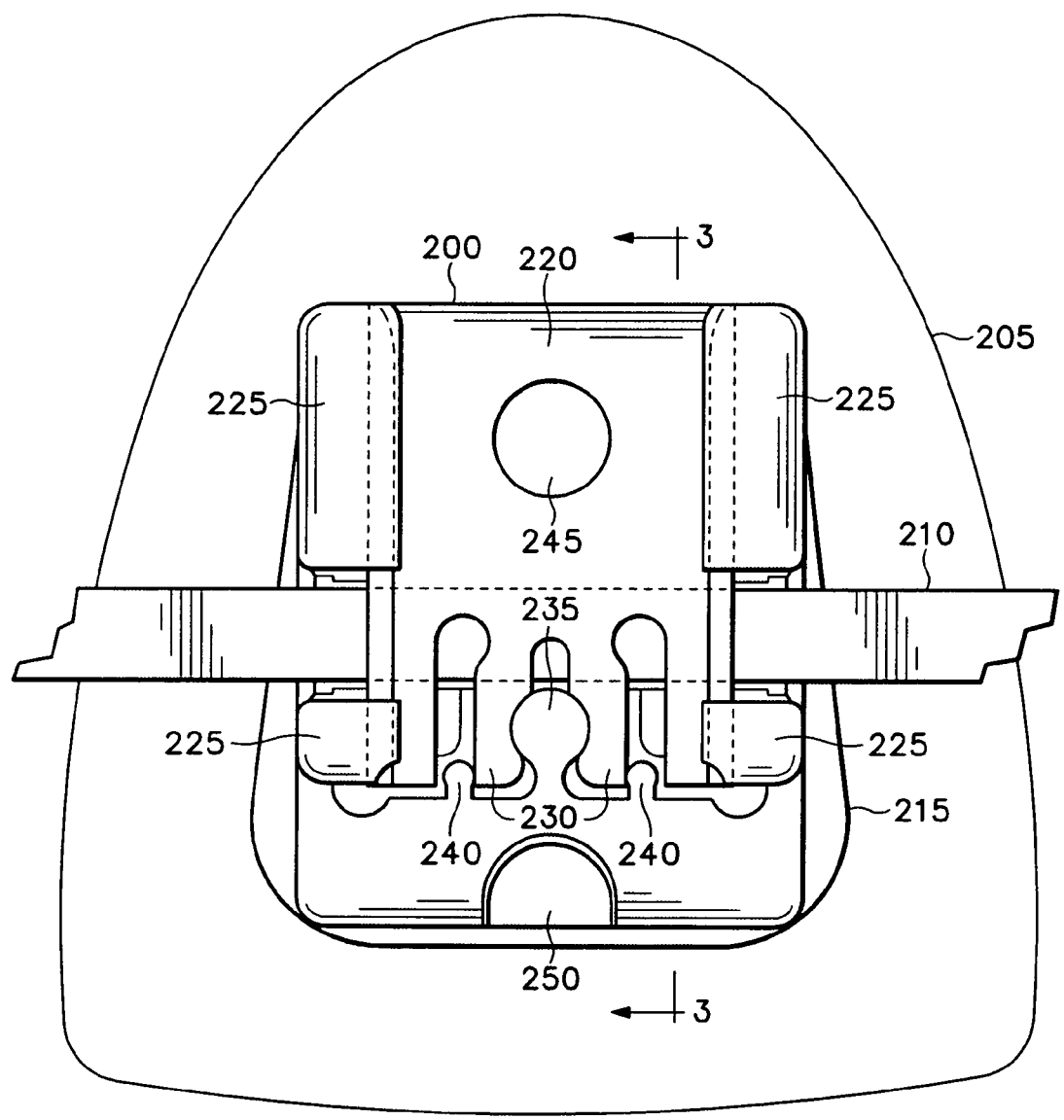
FIG. 2 illustrates an exemplary frontal view of an improved orthodontic bracket placed upon a tooth and engaged with an archwire.

FIG. 2 illustrates an exemplary frontal view of a self-ligating orthodontic bracket 200 placed upon a tooth 205 and engaged with an archwire 210. The bracket 200 is shown mounted to the labial surface of an upper anterior tooth 205 (one of the upper centrals, laterals, or cuspids). However, the bracket 200 may also be mounted to the lingual surface of a tooth 205, and the tooth 205 may comprise any tooth such as one of the upper or lower centrals, laterals, cuspids, bicuspids, molars, and so on.

As shown, the archwire 210 is retained within the self-ligating bracket 200 and runs parallel to the occlusal surface (the cutting or incisal edge) of the tooth 205. Other orientations may be used with the bracket 200. However, this orientation is typical of a straight-wire (or Roth) appliance whereby crown angulation and crown inclination are engineered into the bracket 200 thereby allowing use of an archwire that is "straight" or parallel to the cutting edge of each tooth (when the teeth are positioned in correct orthodontic alignment). Crown angulation is generally the mesial-distal to gingival-occlusal orientation of the tooth and is affected by the mesial-distal orientation of the archwire slot (or slot tip). The crown angulation for the bracket 200 as shown in FIG. 2 is perpendicular. The archwire 210 in FIG. 2 runs along a mesial-distal line parallel to the incisal edge of tooth 205 and is oriented perpendicular to the gingival-occlusal axis (or long axis) of the clinical crown. Other non-perpendicular crown angulations may be engineered into the bracket 200 resulting in a bracket 200 with a rhomboid or parallelogram frontal profile instead of the rectangular frontal profile depicted in FIG. 2.

Crown inclination is generally the labial-lingual to gingival-occlusal orientation of the tooth and is affected by the rotational orientation of the archwire slot (or slot torque)

along the mesial-distal (or archwire) axis. The rotational orientation of the archwire slot will be discussed in greater detail below in the context of axial or sectional views of the bracket along the mesial-distal axis.

Whereas a straight-wire appliance typically includes individually engineered brackets with each bracket having the desired crown inclination (slot torque) and crown angulation (slot tip) for a particular tooth, other techniques may be used which require different orientations. For example, a standard edgewise appliance typically includes brackets having a rectangular profile and an orientation such that the centerline of the bracket is aligned along the gingival-occlusal axis (or long axis) of the clinical crown and perpendicular with the archwire slot. Typically, the brackets in a standard edgewise appliance have archwire slots that are not parallel to the incisal edges of the teeth (when the teeth are positioned in correct orthodontic alignment). Instead, the archwire is angled, bent, and twisted to define the desired position of the teeth.

Still referring to FIG. 2, the mounting base 215 of the bracket 200 may be sized to fit the particular tooth surface 205. For example, the mounting base 215 may be wider at the incisal end of the tooth 205 to match the shape of the tooth surface. The bracket 200 may be bonded to the surface of tooth 205, or, alternatively, to a band assembly (not shown) which is attached to the tooth 205. As shown, the bracket 200 is oriented so that the ligating slide member 220 slideably opens in the gingival direction and closes in the occlusal direction. However, the bracket may be oppositely oriented so that the ligating slide member 220 slideably opens in the occlusal direction and closes in the gingival direction. The ligating slide member 220 is shown in a closed position for retaining the archwire 210.

As in FIG. 1, the ligating slide member 220 may slide within a channel formed between sides 225 and oriented transverse to the archwire slot. The ligating slide member 220 preferably includes one or more coplanar resilient retention features (or mechanism) 230 for holding the ligating slide member 220 in a closed position thereby retaining the archwire 210. The one or more coplanar resilient retention features 230 may comprise resilient portions of the ligating slide member 220 suitably formed to allow coplanar deflection and subsequent locking with one or more mating protrusions 235 and 240. Here, the resilient retention features 230 have been designed to deflect outward in the mesial-distal direction, perpendicular to the (gingival-occlusal) channel formed by sides 225, for lockable engagement with a larger (mating) protrusion 235 and smaller (secondary) protrusions 240. In this configuration, the resilient retention features 230 deflect and engage with the mating protrusions 235 and 240 transverse to and coplanar with the channel formed between sides 225.

More particularly, in one embodiment, the resilient retention features 230 resemble coplanar fingers within the ligating slide member 220 which deflect outward in a mesial-distal direction around a mating protrusion 235 within the bracket 200. As the ligating slide member 220 slides downward (in the occlusal direction), the resilient retention features 230 deflect outward and then return toward their former positions as they lock about the mating protrusion 235. Just before the resilient retention features 230 reach their former positions a small portion of the outer ends of the resilient retention features 230 make contact with the smaller protrusions 240 which improve the (inward and coplanar) locking forces exerted on the resilient retention features 230.

Finally with regard to FIG. 2, the mating protrusion 235, other symmetrical aspects of the bracket 200 such as the sides 225, and the recesses 245 and 250, individually or in combination, provide a visual centerline for the bracket 200 useful to aid the orthodontist in the placement of the bracket 200 upon the tooth 205.

Figure 3:
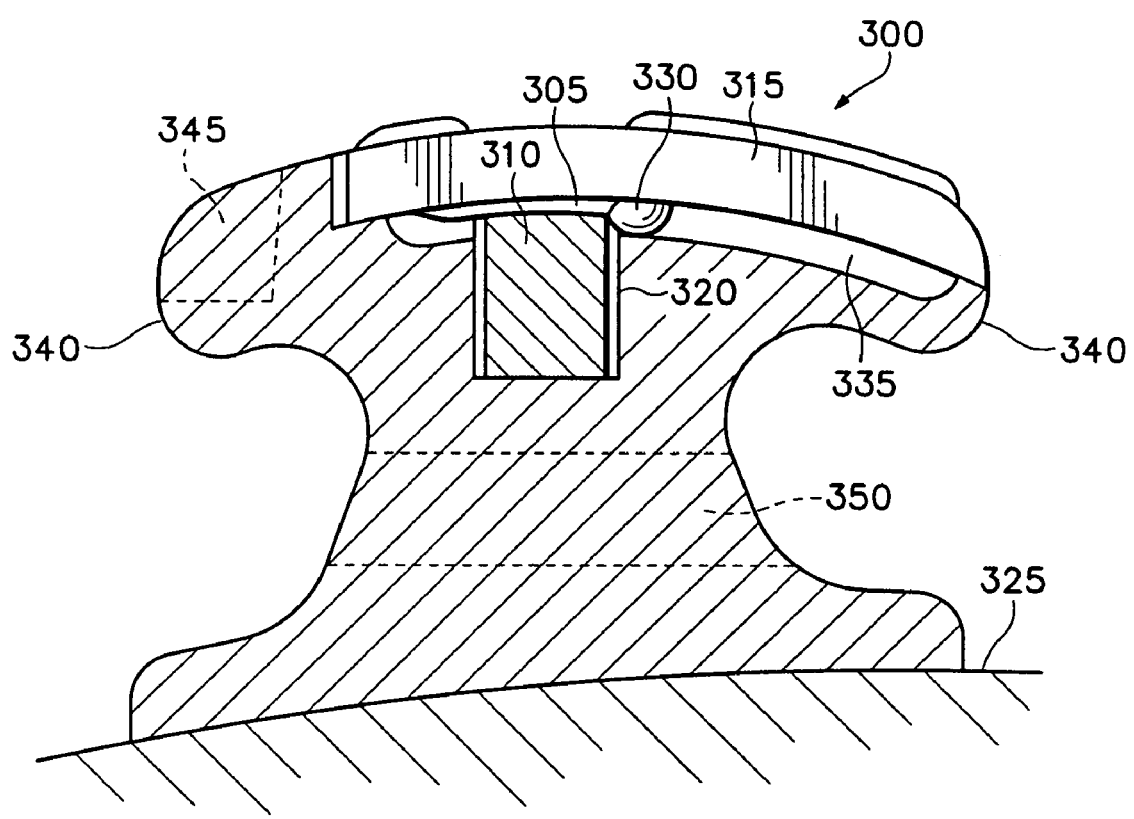
FIG. 3 illustrates a sectional view of an improved orthodontic bracket actively engaged with an archwire according to one embodiment of the invention.

Next, FIG. 3 provides a sectional view (referenced in FIG. 2) of an improved orthodontic bracket 300 with active engagement protrusions 305 for actively engaging an archwire 310, according to one embodiment of the invention. The bracket 300 is shown with a ligating slide member 315 in a closed position for retaining the archwire 310 within the archwire slot 320. The underside of the ligating slide member 315 includes one or more active engagement protrusions 305 that forcibly restrain (or actively engage) the archwire 310 when the ligating slide member 315 is closed over the archwire 310. Active engagement of the archwire 310 within the archwire slot 320 effectively locks the archwire 310 within the archwire slot 320, thus improving mesial-distal control. With active engagement of the archwire 310 the forces exerted from the archwire 310 in the mesial-distal direction may be transmitted to the bracket 300 through the one or more active engagement protrusions 305. For example, a bracket 300 with active engagement may be used adjacent to another bracket without active engagement for closure of a diastema.

Active engagement of the archwire 310 (particularly a rectangular archwire, as shown) within the (rectangular) archwire slot 320 also permits improved control of crown inclination. With the archwire 310 locked into the archwire slot 320, twists along the archwire 310 may be transmitted to the bracket 300 through the one or more active engagement protrusions 305 as well as contacts between the lengthwise edges of the rectangular archwire 310 and the surfaces of the correspondingly rectangular archwire slot 320. As previously mentioned, crown inclination is generally the labial-lingual to gingival-occlusal orientation of the tooth and is affected by the rotational orientation of the archwire slot 320 (or slot torque) along the mesial-distal (or archwire) axis. FIG. 3 shows an axial (or sectional) view of the bracket 300 along the mesial-distal axis. Here, the archwire slot 320 is shown angled (or rotated) slightly such that the labial-lingual sides of the archwire slot 320 (which are normal to the ligating slide member 315) are not perpendicular (or not normal) to the tooth surface 325. This is a typical rotational orientation for the archwire slot used in a straight-wire appliance where slot torque is engineered into the bracket. A standard edgewise appliance, in contrast, typically includes an archwire slot with sides perpendicular to the mounting surface of the tooth.

In addition to the one or more active engagement protrusions 305 which may be formed upon the underside of the ligating slide member 315, one or more slide member stops 330 may be formed upon the underside of the ligating slide member 315 for preventing the ligating slide member 315 from sliding beyond the limits of a slide path 335 formed as a recessed area within the channel.

Other features of the bracket 300 illustrated in FIG. 3 include the convex shape of the ligating slide member 315 and other features defining the outer most surfaces of the bracket 300, a pair of tie wings 330 extending transverse to the archwire slot 320 (one extending in a gingival direction and the other extending in an occlusal direction), and a recessed area 335 (indicated by broken lines) corresponding to the recess 250 shown in FIG. 2. As previously mentioned, the convex gingival-occlusal contour of the bracket 300 improves comfort for the appliance-wearing patient. The tie wings 330 provide additional utility and flexibility for the orthodontist in applications where the use of standard elastomeric ligatures or other attachments requiring tie wings may be desired.

In one embodiment, a vertical slot 350 may be incorporated into the bracket 300. The vertical slot 350 (indicated by broken lines) is shown oriented transverse to the archwire slot 320 in a gingival-occlusal direction and positioned between the archwire slot 320 and the mounting base of the bracket 300. Such a vertical slot (such as vertical slot 350) allows placement of auxiliaries in the vertical slot to facilitate tooth inclination, angulation, and rotation, if needed.

Figure 4:
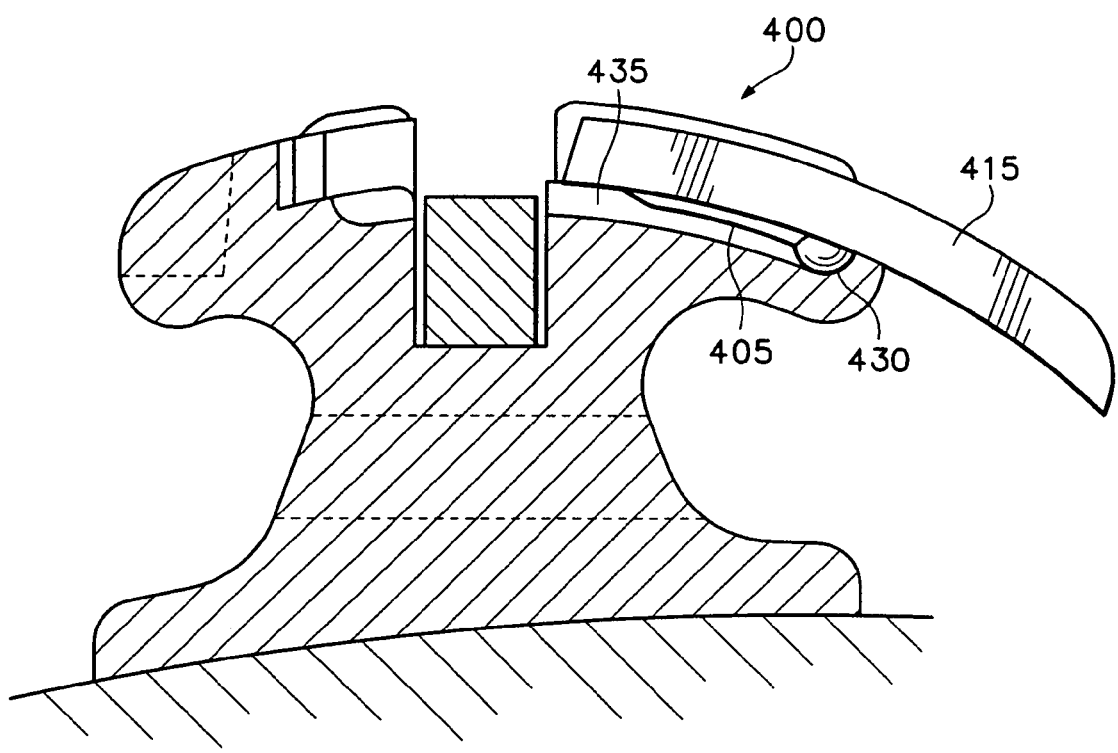
FIG. 4 illustrates a sectional view of an improved orthodontic bracket with a ligating slide member in an open position, according to one embodiment of the invention.

FIG. 4 illustrates a sectional view of an improved orthodontic bracket 400 with one or more active engagement protrusions 405 and a ligating slide member 415 in a fully opened position, according to one embodiment of the invention. In the fully opened position, the one or more slide member stops 430 formed upon the underside of the ligating slide member 415 prevents the ligating slide member 415 from sliding beyond the end of the slide path 435.

Figure 5:
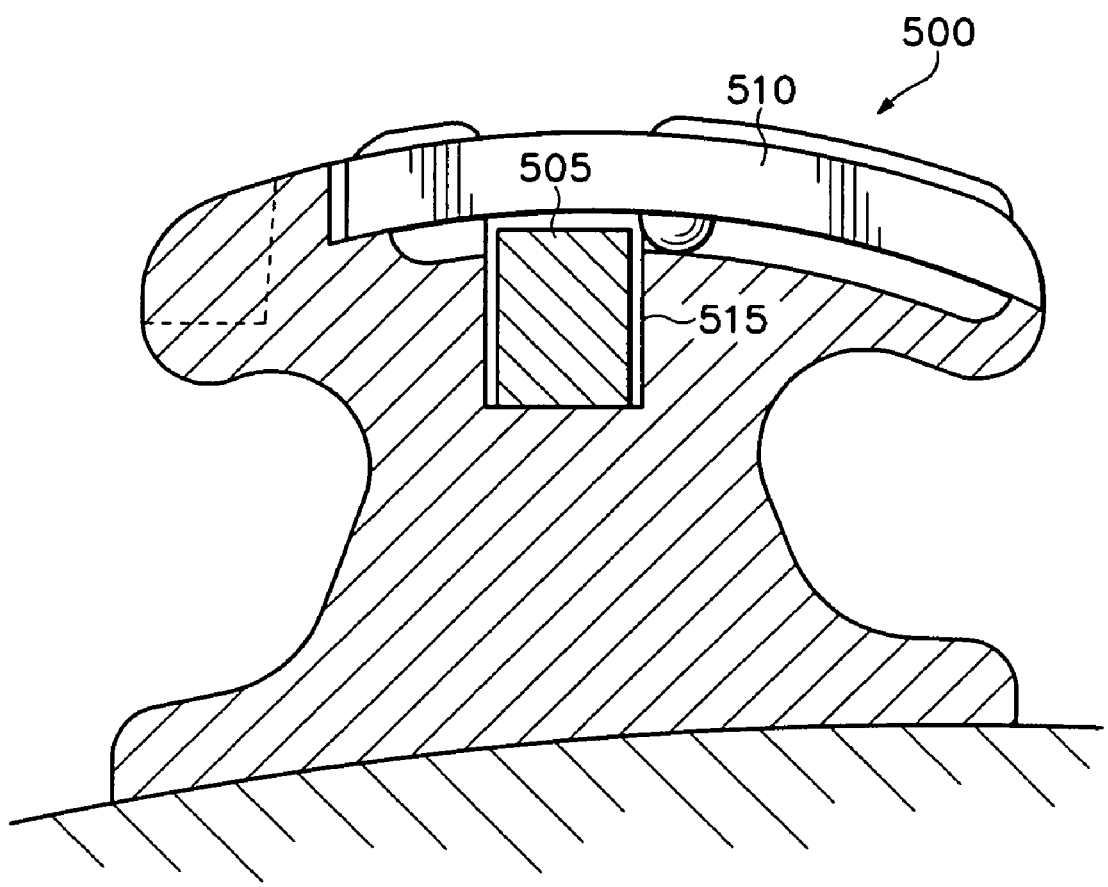
FIG. 5 illustrates a sectional view of an improved orthodontic bracket passively engaged with an archwire according to one embodiment of the invention.

FIG. 5 illustrates a sectional view of an improved orthodontic bracket 500 passively engaged with an archwire 505 according to one embodiment of the invention. Whereas the bracket 400 shown in FIG. 4 represents the bracket 300 with the ligating slide member shown in a fully opened position, the bracket 500 represents a similar sectional view of a different bracket. The bracket 500 includes a ligating slide member 510 illustrated in a closed position covering the archwire 505 such that the archwire 505 is not forcibly restrained within the archwire slot 515. Here, the archwire 505 is retained within the archwire slot 515 and allowed to move within the archwire slot 515. Hence, the bracket 500 is said to be passively engaged with the archwire 505. As previously mentioned, a bracket 500 with passive engagement may be used for closure of a diastema. For instance, elastics may be used to urge teeth together where the brackets bonded to those teeth have freedom to move along the mesial-distal (archwire) axis.

Figure 6:
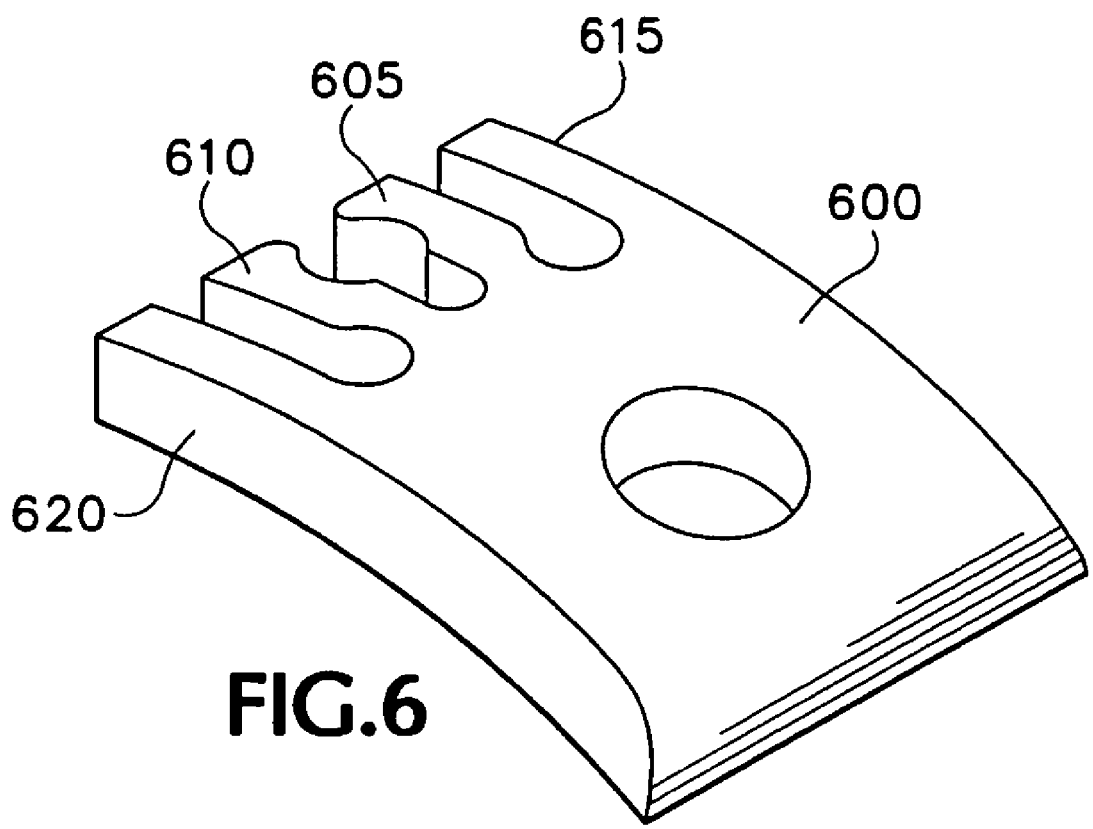
FIG. 6 illustrates an isometric top view of a ligating slide member according to one embodiment of the invention.
Figure 7:
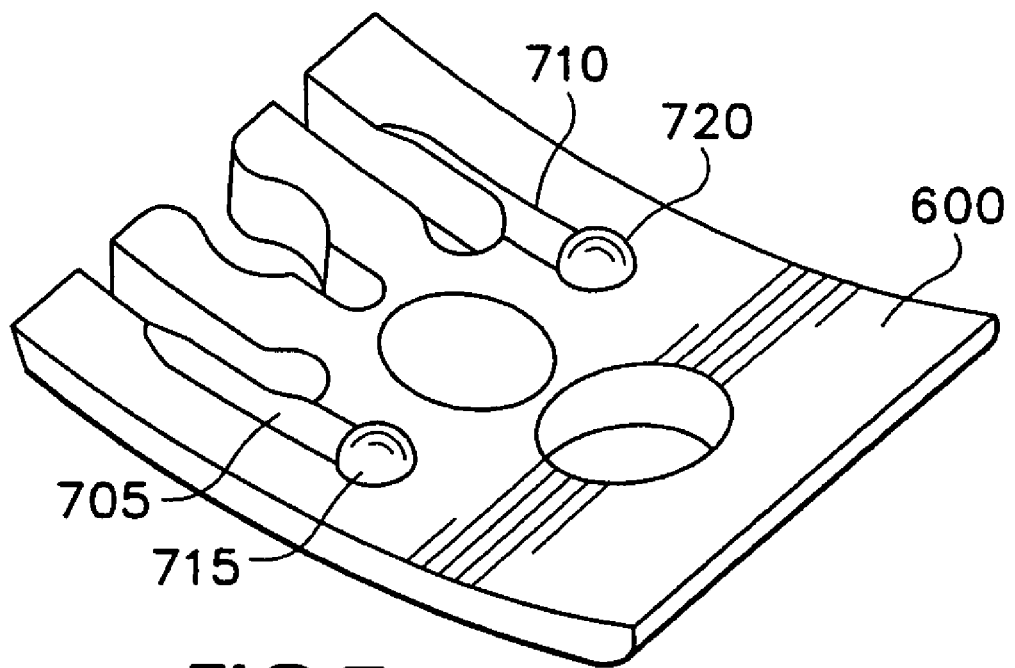
FIG. 7 illustrates an isometric bottom view of a ligating slide member according to one embodiment of the invention.

Next, FIGS. 6 and 7 illustrate top and bottom views, respectively, of a ligating slide member according to one embodiment of the invention. The ligating slide member 600 comprises a convex shaped archwire slot cover with resilient retention features 605 and 610 at one end. The resilient retention features 605 and 610 may comprise different shapes from those illustrated in FIG. 6. However, the resilient retention features 605 and 610 are preferably shaped to allow deflection transverse to and coplanar with the direction of travel of the ligating slide member 600 so as to permit deflection about one or more mating protrusion features formed within the receiving (or closing) end of the channel holding the ligating slide member 600. As shown, the resilient retention features 605 and 610 comprise coplanar fingers formed at the locking end the ligating slide member 600. The resilient retention feature 605 is designed to deflect outward from the centerline of the ligating slide member 600 toward the outer edge 615. Likewise but with opposite direction, the resilient retention feature 610 is designed to deflect outward from the centerline of the ligating slide member 600 toward the outer edge 620. Both resilient retention features 605 and 610 spring back toward their former shapes prior to deflection thereby lockably retaining the ligating slide member 600 in a closed position.

The underside of the ligating slide member 600 is illustrated in FIG. 7. The ligating slide member may include elongated protrusions 705 and 710 for actively engaging an archwire within the archwire slot of a bracket (such as bracket 300). The ligating slide member preferably includes slide stop protrusions 715 and 720 for retaining the ligating slide member 600 in an open position, exposing the archwire slot of a bracket (such as bracket 300).

Figure 8:
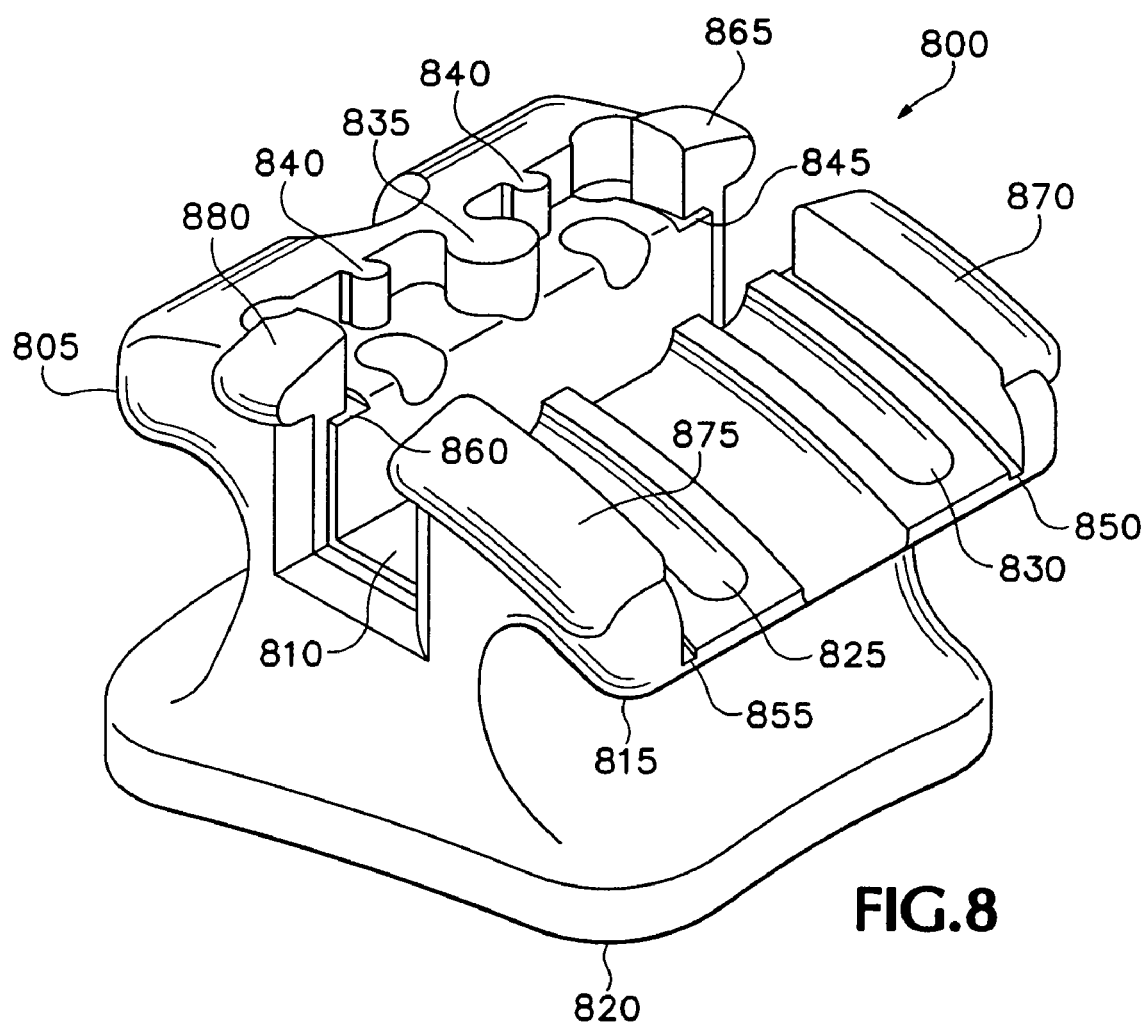
FIG. 8 illustrates an isometric view of an improved orthodontic bracket with its ligating slide member removed, according to one embodiment of the invention.

FIG. 8 illustrates an isometric view of an improved orthodontic bracket with its ligating slide member removed, according to one embodiment of the invention. The bracket body 800, as shown, incorporates a convex gingival-occlusal contour extending from the tie wing 805 across the archwire slot 810 to the tie wing 815. Although not shown, in one embodiment, the bracket body 800 incorporates a convex mesial-distal contour extending along the archwire slot 810. The mounting base 820 may be contoured in either or both gingival-occlusal and mesial-distal directions to improve adhesion to a tooth surface.

The slide paths 825 and 830, in one embodiment, are sized to receive the slide member stops 715 and 720 as well as (particularly where an active engagement ligating slide member is used) the elongated protrusions 705 and 710. The slide paths 825 and 830 preferably extend to the other side of the archwire slot 810 to accommodate the elongated protrusions 705 and 710 when the ligating slide member is in a closed position. The larger mating protrusion 835 and smaller locking protrusions 840 may be as described previously and illustrated in FIGS. 1 and 2.

Still referring to FIG. 8, relief grooves 845, 850, 855, and 860 may be formed into the bracket base 800 to facilitate a coining operation to capture and retain a ligating slide member within a dovetail channel formed by crimping the channel sides 865, 870, 875, and 880 inward. The relief grooves 845, 850, 855, and 860 are formed lengthwise along the edges of the channel at the base of the channel sides 865, 870, 875, and 880.

Figure 9:
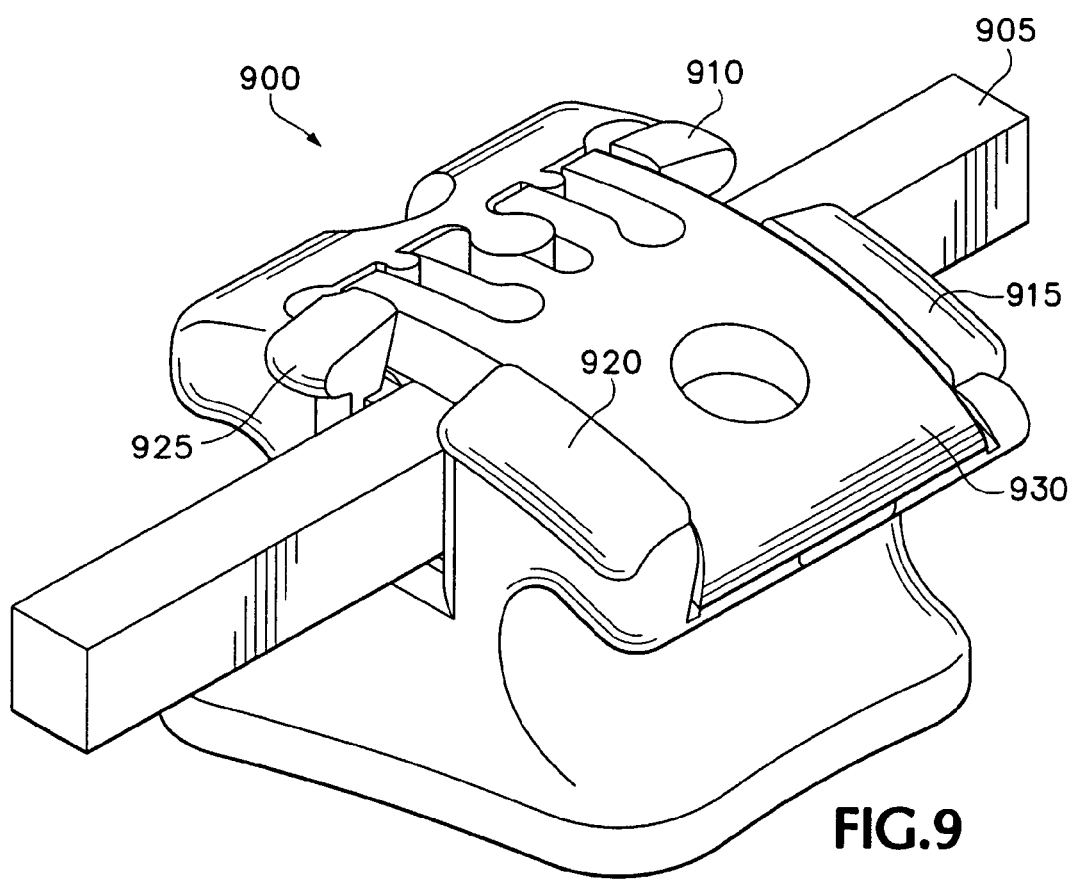
FIG. 9 illustrates an isometric view of an improved orthodontic bracket engaged with an archwire according to one embodiment of the invention.

FIG. 9 illustrates an isometric view of an improved orthodontic bracket 900 engaged with a rectangular archwire 905 according to one embodiment of the invention. The channel sides 910, 915, 920, and 925 have been crimped inward to capture a ligating slide member 930. The ligating slide member 930 may be lockably retained in a closed position as previously described and illustrated in FIGS. 1 and 2.

Figure 10:
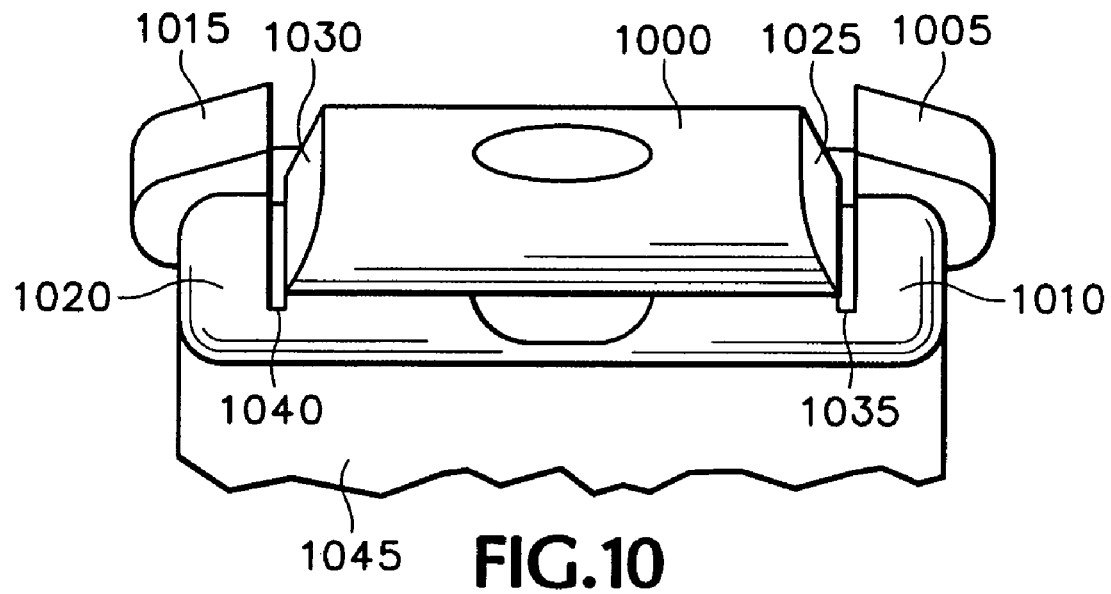
FIG. 10 illustrates a ligating slide member placed within a channel of an improved orthodontic bracket, according to one embodiment of the invention.
Figure 11:
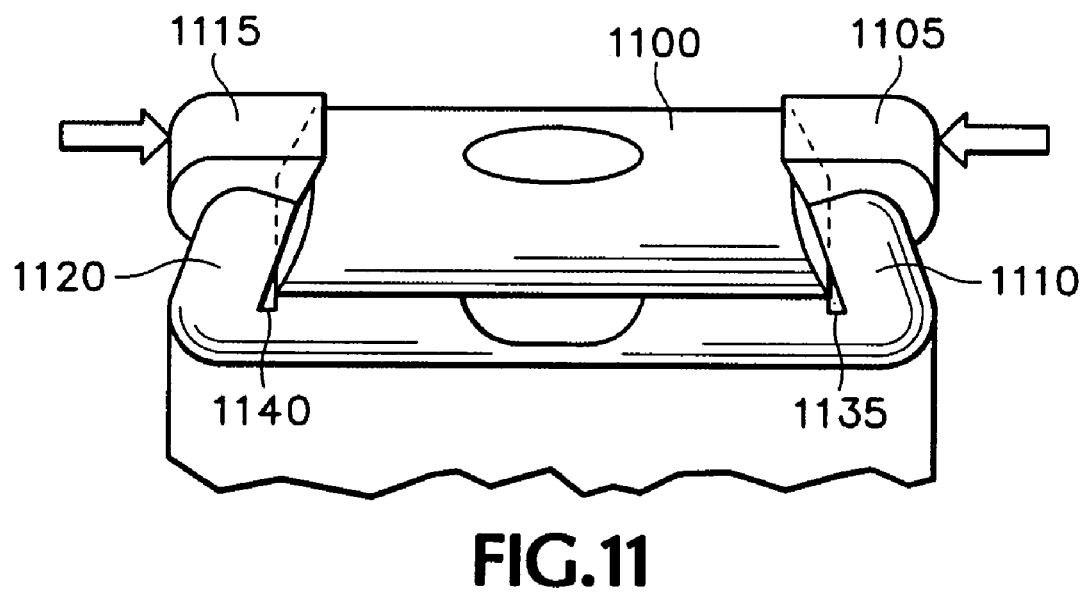
FIG. 11 illustrates a ligating slide member placed within a channel of an improved orthodontic bracket following a coining operation for retaining the ligating slide member within the channel, according to one embodiment of the invention.

Next, FIGS. 10 and 11 illustrate exemplary details pertaining to a channel within which a ligating slide member may be slideably retained. FIG. 10 illustrates a ligating slide member 1000 placed within a channel, according to one embodiment of the invention. The channel comprises sides 1005, 1010, 1015, and 1020 which are then crimped inward to slideably mate with the correspondingly tapered edges 1025 and 1030 of the ligating slide member 1000. Relief grooves 1035 and 1040 may be formed lengthwise within the channel proximate to the lengthwise transition point where sides 1005, 1010, 1015, and 1020 extend upward from the bracket base 1045.

FIG. 11 illustrates a ligating slide member 1100 placed within a channel of an improved orthodontic bracket following a coining operation for retaining the ligating slide member 1100 within the channel, according to one embodiment of the invention. As shown, the sides 1105, 1110, 1115, and 1120 are crimped inward to slideably mate with the correspondingly tapered edges of the ligating slide member 1100. The result comprises a slide-type joint (sometimes referred to as a dovetail joint or dovetail shaped joint) between the sides 1105, 1110, 1115, and 1120 and the ligating slide member 1110. The relief grooves 1135 and 1140 may be slightly reduced in size after the coining operation to crimp the sides 1105, 1110, 1115, and 1120 inward. Among other benefits, the relief groves improve the dimensional quality of the dovetail shaped channel and provide additional clearance within which the ligating slide member 1110 may slide within the channel.

As commonly practiced in orthodontic treatment, brackets may be fabricated for a particular patient by prescription. The brackets may be engineered to include the appropriate slot torque and slot tip for each individual tooth for the particular patient. For example, specifically engineered brackets may be fabricated for the upper left central, the upper left lateral, the upper left cuspid, and so forth moving distally toward the upper left molars (using Palmer's notation for designating individual teeth). Each bracket typically incorporates a particular slot torque and slot tip as well as other features as may be needed. For instance, the bracket for the upper left cuspid may include a slot tip of, perhaps, 90 and include a ball hook for use with elastics or other features of the orthodontic appliance. Such a bracket may have the features as in FIG. 12.

Figure 12:
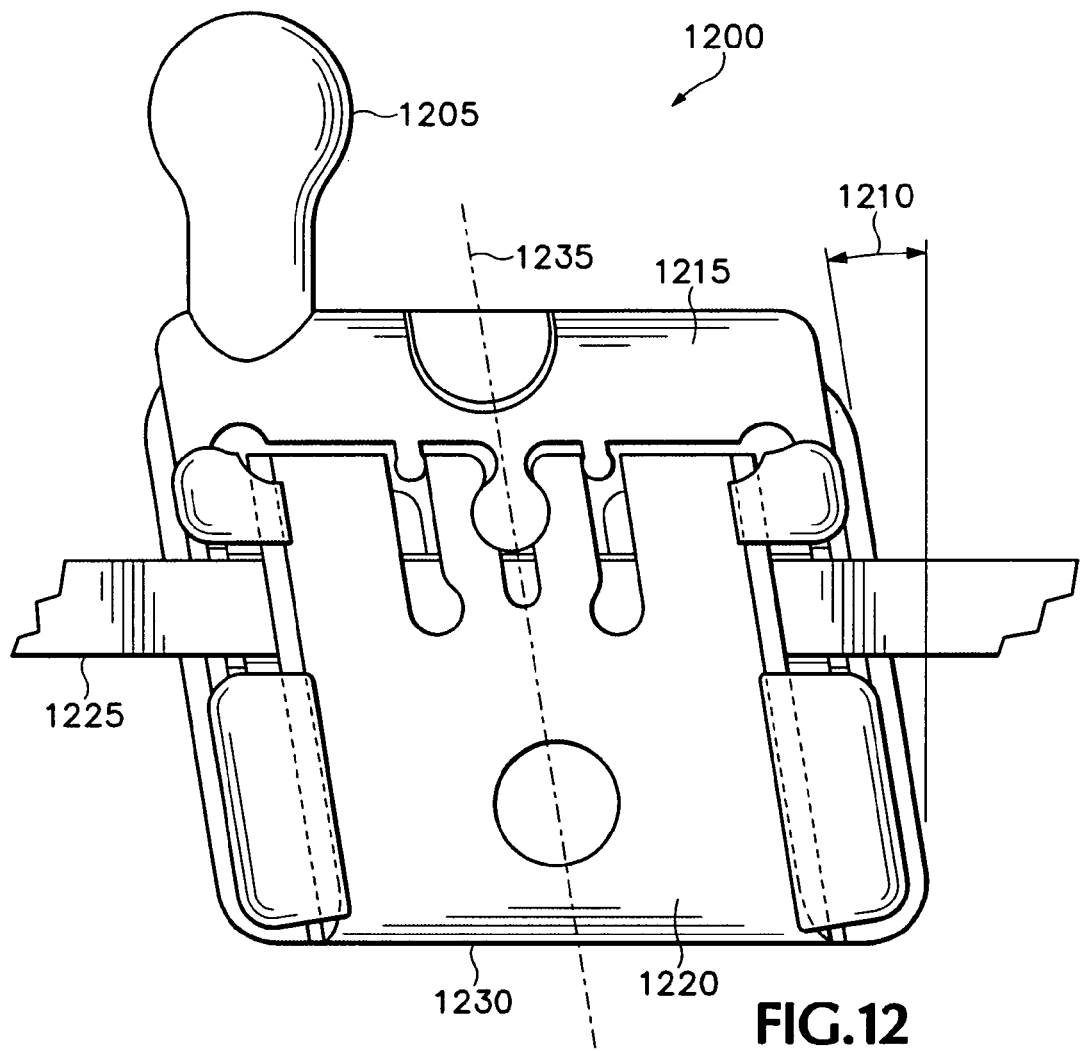
FIG. 12 illustrates a top view of a parallelogram version of an improved orthodontic bracket with a ball hook, according to one embodiment of the invention.

As shown, FIG. 12 illustrates a top view of a parallelogram version of an improved orthodontic bracket 1200 with a ball hook 1205, according to one embodiment of the invention. The bracket 1200 includes an engineered slot tip 1210 so that the bracket parallels tooth angulation for easy placement. The ball hook 1205 is shown formed upon the mesial gingival portion of the gingival tie wing 1215. The ligating slide member 1220 is shown oriented to open in a downward direction toward the incisal edge of the tooth (as opposed to previously illustrated brackets which were oriented to open in the gingival direction, toward the gums). The archwire 1225 and occlusal edge 1230 of the bracket 1200 are both parallel to the incisal edge of the tooth, and the centerline 1235 of the bracket 1200 aligns with the long axis of the clinical crown.

Figure 13:
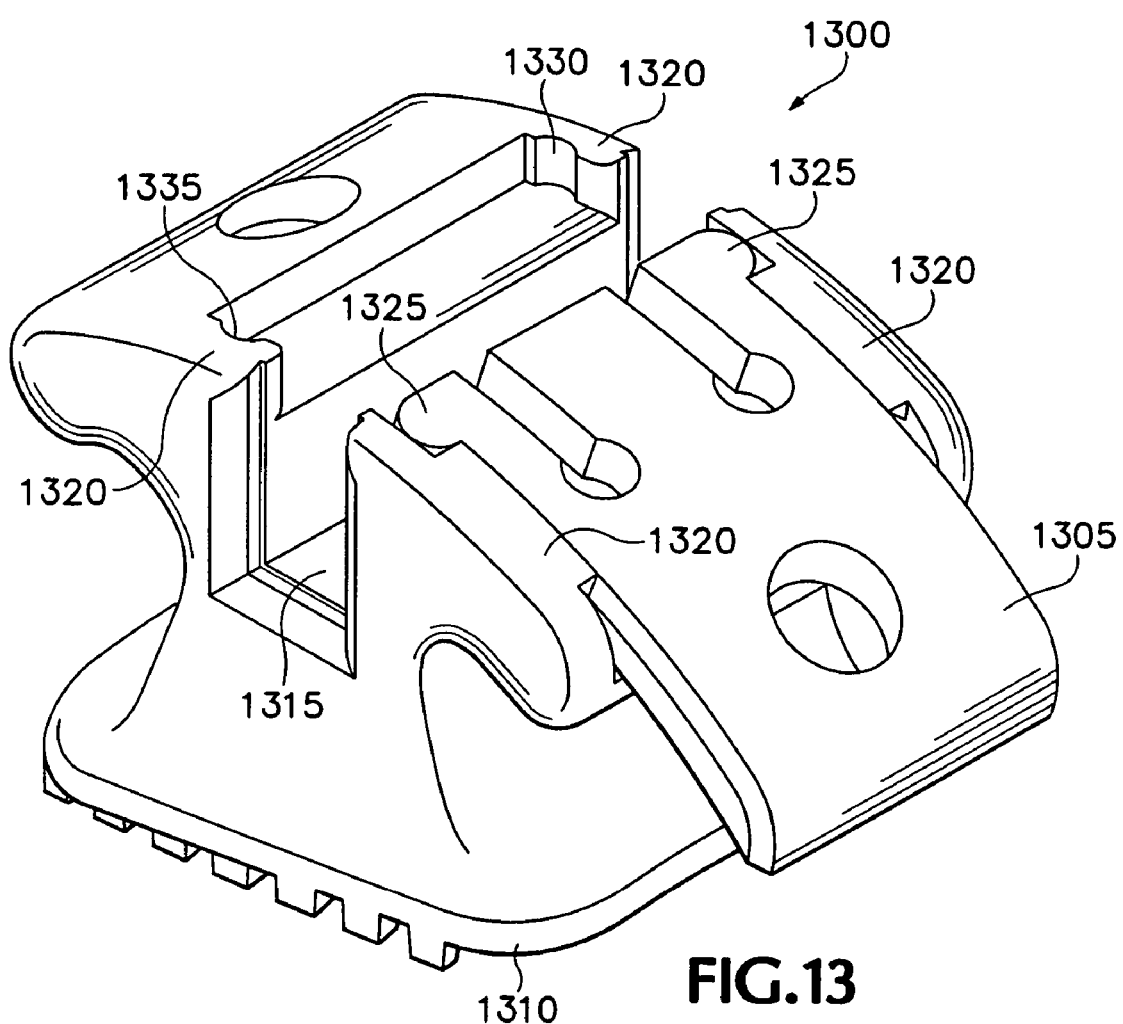
FIG. 13 illustrates an isometric view of an improved orthodontic bracket with a ligating slide member in an open position, according to one embodiment of the invention.

As will be appreciated, variations of the improved orthodontic bracket described herein may be apparent. For example, FIG. 13 illustrates an isometric view of an improved orthodontic bracket 1300 with a ligating slide member 1305 in an open position, according to one embodiment of the invention. The self-ligating orthodontic bracket 1300 includes a mounting base 1310 for attachment to a tooth surface, an archwire slot 1315 formed upon the mounting base 1310 and sized for receiving an orthodontic archwire (not shown), and the ligating slide member 1305 (shown in an open position) for retaining an orthodontic archwire within the archwire slot 1315. The ligabng slide member 1305 may slide within a channel formed between sides 1320 and oriented transverse to the archwire slot 1315. The ligating slide member 1305 preferably includes one or more coplanar resilient retention features 1325 for holding the ligating slide member 1305 in a closed position thereby retaining an orthodontic archwire within the archwire slot 1315.

As shown in FIG. 13, the one or more coplanar resilient retention features (or mechanism) 1325 may comprise resilient portions of the ligating slide member 1305 suitably formed to allow coplanar deflection and subsequent locking with one or more mating indents 1330 and 1335. Here, the resilient retention features 1325 have been designed to deflect inward, perpendicular to the channel formed by sides 1320, for engagement with indents 1330 and 1335. In this configuration, the resilient retention features 1325 deflect and engage with the mating indents 1330 and 1335 transverse to and coplanar with the channel formed between sides 1320. Consequently, forces exerted normal to the ligating slide member 1305, as may arise due to movement of an archwire retained within the archwire slot 1315, are not likely to affect the retention of the archwire within the archwire slot 1315. Thus, the self-ligating orthodontic bracket 1300 more securely retains an archwire than other bracket designs.

Slide stops to prevent the ligating slide member 1305 from pulling completely away from the rest of the bracket 1300 may be provided by suitably formed sides 1320 as shown in FIG. 13 or as described and illustrated FIGS. 4, 5, 7, and 8. Also referring back to FIGS. 4, 5, 7, and 8, the bracket 1300 may incorporate protrusions formed upon the ligating slide member 1305 and corresponding relief areas for active engagement with an archwire within archwire slot 1315.

Although not shown, the bracket 1300 may incorporate sides 1320 that may be crimped inward as with sides 1105, 1110, 1115, and 1120 in FIG. 11. Further, the mounting base 1310 may include an uneven or rough bonding surface 1340 as shown. As will be appreciated, many or all of the foregoing features may be incorporated in to the bracket 1300. For instance, the bracket 1300 may include a ball hook attachment to one of the tie wings such as tie wing 1345, a vertical slot transverse to the archwire slot 1315 and between the archwire slot 1315 and the mounting base 1310, and a parallelogram shape as in FIG. 12.

The improved orthodontic bracket described herein may comprise any of a wide variety of materials suitable for use in an orthodontic appliance. Such materials have commonly included plastics, ceramics, stainless steel, titanium, or other metal alloys. The bracket preferably comprises a biocompatible material with corrosion resistive properties, and the bracket preferably comprises materials which may be formed into the structure shown yet maintain suitable strength characteristics for retaining commonly used orthodontic archwires or other components of an orthodontic appliance.

Nickel may be the most common metal associated with contact dermatitis in orthodontics. Recent figures suggest that perhaps 10% of patients are sensitive to nickel. Nevertheless, nickel-containing metal alloys, such as nickel-titanium and stainless steel, are widely used in orthodontic appliances. Nickel-titanium alloys may have nickel contents above 50% and may potentially release enough nickel in the oral environment to elicit manifestations of an allergic reaction. Stainless steel has a much lower nickel content, perhaps around 8%, and, because the nickel is bound in a crystal lattice within stainless steel, the nickel may be less available to react. Consequently, stainless steel orthodontic components may be less likely to cause nickel hypersensitivity.

However, because of the remaining uncertainty regarding a particular patient's sensitivity to nickel, it may be desireable to provide nickel-free orthodontic brackets to avoid nickel hypersensitivity altogether. Therefore, the improved orthodontic bracket described herein preferably comprises a nickel-free material. In one embodiment, the bracket comprises a nickel-free cobalt-chromium alloy.

Several methods may be used to manufacture the improved orthodontic bracket described herein. For example, the bracket may be cast, machined, injection molded and so on. Injection molding of plastics may be used as may be ceramic injection molding (CIM) or metal injection molding (MIM) depending upon the materials chosen. Further, the bracket may comprise multiple assembled components. For instance, the bracket may comprise the assembly of a formed bracket body and a formed ligating slide member, the ligating slide member retained within the channel of the bracket body following a coining operation whereby the channel sides are crimped inward along the sides of the ligating slide member (forming a dovetail joint). A ball hook may be welded to the bracket assembly, and a wire mesh may be adhered to the mounting base of the bracket to improve its bonding surface.

In one embodiment, the improved orthodontic bracket base is formed of nickel-free cobalt chromium using a metal injection molding process whereby the ligating slide member is similarly constructed and attached using a coining operation to crimp the sides of the bracket base (bracket body). In one embodiment, the improved orthodontic bracket comprises a one-piece molded bracket body and a one-piece molded ligating slide member, the ligating slide member assembled to the bracket body using the aforementioned coining operation.

As described herein, the present invention provides an improved self-ligating orthodontic bracket. According to one embodiment, the improved orthodontic bracket may include a mounting base for attachment to a tooth surface, an archwire slot formed upon the base and sized for receiving an orthodontic archwire, a channel formed upon the base and transversely oriented to the archwire slot, and a ligating slide member slideably retained within the channel and closeable over the archwire slot for retaining the orthodontic archwire therein, wherein the ligating slide member includes at least one coplanar resilient retention mechanism for exerting retention forces coplanar with the ligating slide member for holding the ligating slide member in a closed position. In one embodiment, the improved orthodontic bracket comprises a bracket with a ligating slide member slideably retained within a dovetail shaped channel.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

What is claimed is:

1. An improved self-ligating orthodontic bracket, comprising:
   a mounting base for attachment to a tooth surface;
   an archwire slot formed upon said base and sized for receiving an orthodontic archwire;
   a channel formed upon said base and transversely oriented to said archwire slot; and
   a ligating slide member slideably retained within said channel and moveable along a path of travel defined by said channel between an open position where the ligating slide member allows access to the archwire slot and a closed position projecting over said archwire slot for retaining said orthodontic archwire therein, said ligating slide member and said base cooperatively having at least one resilient retention mechanism aligned in parallel relation to said ligating slide member, said resilient retention mechanism resiliently deflecting in a direction transverse to said path of travel and in a plane parallel with said ligating slide member and exerting retention forces in a direction generally coplanar with said ligating slide member, to hold said ligating slide member in said closed position.

2. The bracket of claim 1, wherein said channel is defined between sides of said channel crimped inward forming a dovetail shaped channel.

3. The bracket of claim 2, wherein said channel includes relief grooves formed lengthwise along the base of said sides of said channel.

4. The bracket of claim 1, wherein said ligating slide member further comprises at least one engagement protrusion for restrainably engaging said orthodontic archwire within said archwire slot.

5. The bracket of claim 1, wherein features of said bracket define a centerline transverse to said archwire slot and useful as a visual aid for positioning said bracket on said tooth surface.

6. The bracket of claim 1, further comprising a vertical slot transverse to said archwire slot and formed between said archwire slot and a tooth bonding surface of said mounting base, said tooth bonding surface for bonding said bracket to said tooth surface.

7. The bracket of claim 1, further comprising at least one pair of tie wings formed upon said base transverse to said archwire slot.

8. The bracket of claim 1, wherein said ligating slide member includes one or more portions configured to deflect outwardly perpendicular to said path of travel to engage a mating protrusion extending from said bracket body.

9. The bracket of claim 1, wherein said bracket comprises an injection molded bracket body.

10. The bracket of claim 1, wherein said resilient retention mechanism includes a slot parallel with said path of travel and a projection received in said slot, said slot and projection mating to retain said ligating slide member in said closed position.

11. The bracket of claim 1, wherein said ligating slide member includes a recess for slideably manipulating said ligating slide member within said channel using an orthodontic tool.

12. The bracket of claim 1, wherein said bracket includes an indent feature opposite said archwire slot from said ligating slide member when said ligating slide member is in an open position exposing said archwire slot, said indent feature for slideably manipulating said ligating slide member within said channel using an orthodontic tool.

13. The bracket of claim 1, wherein surfaces of said bracket opposite a tooth bonding surface of said mounting base comprise a convex shape for improving patient comfort, said tooth bonding surface for bonding said bracket to said tooth surface.

14. The bracket of claim 1, wherein said ligating slide member and said channel comprise a convex shape.

15. The bracket of claim 1, wherein said ligating slide member comprises at least one slide stop protrusion for holding said ligating slide member within said channel when said ligating slide member is in a fully open position exposing said archwire slot.

16. The bracket of claim 1, wherein said mounting base comprises a tooth bonding surface having grooves for improving adhesion to said tooth surface.

17. The bracket of claim 1, wherein said bracket comprises a one-piece injection molded bracket body having said ligating slide member slideably retained within said channel, said channel defined between sides of said channel crimped inward forming a dovetail shaped channel.

18. An improved self-ligating orthodontic bracket, comprising: a mounting base for attachment to a tooth surface; an archwire slot formed upon said base and sized for receiving an orthodontic archwire; a channel formed upon said base and transversely oriented to said archwire slot; and a ligating slide member slideably retained within said channel and movable in said channel along a path of travel defined by said channel between an open position allowing access to said archwire slot and a closed position over said archwire slot for retaining said orthodontic archwire therein, said ligating slide member and said base cooperatively having at least one resilient retention mechanism aligned with said path of travel and exerting retention forces in a direction coplanar with said ligating slide member and, thereby, holding said ligating slide member in said closed position, said at least one resilient retention mechanism having a finger-like shape deflecting in a direction transverse to said path of travel and coplanar with said ligating slide member around a mating protrusion formed at a closing end of said channel.

19. The bracket of claim 18, wherein said finger-like shape makes slight contact with a secondary protrusion formed at said closing end of said channel, said secondary protrusion improving coplanar locking forces exerted on said finger-like shape.

20. The bracket of claim 18, wherein said channel is defined between sides of said channel crimped inward forming a dovetail shaped channel.

21. The bracket of claim 20, wherein said channel includes relief grooves formed lengthwise along the base of said sides of said channel.

22. The bracket of claim 18, wherein said ligating slide member further comprises at least one active engagement protrusion for restrainably engaging said orthodontic archwire within said archwire slot.

23. The bracket of claim 18, wherein features of said bracket define a centerline transverse to said archwire slot and useful as a visual aid for positioning said bracket on said tooth surface.

24. The bracket of claim 18, further comprising a vertical slot defined by said mounting base transverse to said archwire slot and formed between said archwire slot and a tooth bonding surface of said mounting base, said tooth bonding surface for bonding said bracket to said tooth surface.

25. The bracket of claim 18, further comprising at least one pair of tie wings formed upon said base.

26. The bracket of claim 18, wherein said bracket comprises a biocompatible material.

27. The bracket of claim 18, wherein said bracket comprises an injection molded bracket body.

28. The bracket of claim 18, wherein said bracket comprises a cobalt chromium alloy.

29. The bracket of claim 18, wherein said ligating slide member includes a recess for slideably manipulating said ligating slide member within said channel using an orthodontic tool.

30. The bracket of claim 18, wherein said mounting base includes an indent feature opposite said archwire slot from said ligating slide member when said ligating slide member is in an open position exposing said archwire slot, said indent feature facilitating slidable manipulation of said ligating slide member within said channel using an orthodontic tool.

31. The bracket of claim 18, wherein surfaces of said bracket opposite a tooth bonding surface of said mounting base comprise a convex shape for improving patient comfort, said tooth bonding surface for bonding said bracket to said tooth surface.

32. The bracket of claim 18, wherein said ligating slide member and said channel comprise a convex shape.

33. The bracket of claim 18, wherein said ligating slide member comprises at least one slide stop protrusion for holding said ligating slide member within said channel when said ligating slide member is in said open position exposing said archwire slot.

34. The bracket of claim 18, wherein said mounting base comprises a tooth bonding surface having grooves for improving adhesion to said tooth surface.

35. The bracket of claim 18, wherein said bracket comprises a one-piece injection molded bracket body having said ligating slide member slideably retained within said channel, said channel defined between sides of said channel crimped inward forming a dovetail shaped channel.

36. An improved self-ligating orthodontic bracket, comprising: a mounting base for attachment to a tooth surface; an archwire slot formed upon said base and sized for receiving an orthodontic archwire; a channel formed upon said base and transversely oriented to said archwire slot; and a ligating slide member slideably retained within said channel and moveable along a path of travel defined by said channel between a closed position projecting over said archwire slot for retaining said orthodontic archwire therein and an open position clear of said archwire slot, said base having sides defining said channel for receiving said ligating slide member, said ligating slide member and said base cooperatively having at least one resilient retention mechanism resiliently deflecting in a direction transverse to said path of travel and in a plane parallel to said ligating slide member and exerting retention forces in a direction generally coplanar with said ligating slide member to hold said ligating slide member in said closed position.

37. The bracket of claim 36, wherein said channel includes relief grooves formed lengthwise along a junction of said base and said sides of said channel.

38. The bracket of claim 36, wherein said ligating slide member further comprises at least one active engagement protrusion for restrainably engaging said orthodontic archwire within said archwire slot.

39. The bracket of claim 36, wherein features of said bracket define a centerline transverse to said archwire slot and useful as a visual aid for positioning said bracket on said tooth surface.

40. The bracket of claim 36, further comprising a vertical slot defined in said base transverse to said archwire slot and formed between said archwire slot and a tooth bonding surface of said mounting base, said tooth bonding surface for bonding said bracket to said tooth surface.

41. The bracket of claim 36, further comprising at least one pair of tie wings formed upon said base transverse to said archwire slot.

42. The bracket of claim 36, wherein said ligating slide member includes one or more portions configured to deflect outwardly perpendicular to said path of travel to engage a mating protrusion extending from said bracket body.

43. The bracket of claim 36, wherein said bracket comprises an injection molded bracket body.

44. The bracket of claim 36, wherein said resilient retention mechanism includes a slot parallel with said path of travel and a projection received in said slot, said slot and projection mating to retain said ligating slide member in said closed position.

45. The bracket of claim 36, wherein said ligating slide member includes a recess for slideably manipulating said ligating slide member within said channel using an orthodontic tool.

46. The bracket of claim 36, wherein said bracket includes an indent feature opposite said archwire slot from said ligating slide member when said ligating slide member is in an open position exposing said archwire slot, said indent feature for slideably manipulating said ligating slide member within said channel using an orthodontic tool.

47. The bracket of claim 36, wherein surfaces of said bracket opposite a tooth bonding surface of said mounting base comprise a convex shape for improving patient comfort, said tooth bonding surface for bonding said bracket to said tooth surface.

48. The bracket of claim 36, wherein said ligating slide member and said channel comprise a convex shape.

49. The bracket of claim 36, wherein said ligating slide member comprises at least one slide stop protrusion for holding said ligating slide member within said channel when said ligating slide member is in a fully open position exposing said archwire slot.

50. The bracket of claim 36, wherein said mounting base comprises a tooth bonding surface having grooves for improving adhesion to said tooth surface.

51. The bracket of claim 36, wherein said bracket comprises a one-piece injection molded bracket body having said ligating slide member slideably retained within said channel.

52. A self ligating orthodontic bracket comprising:
- a mounting base for attachment to a tooth surface, said mounting base defining an archwire slot having an opening facing away from said tooth for receiving an orthodontic archwire and a channel generally perpendicular to said archwire slot; and
- a ligating slide member retained in said channel and moveable along a path of travel between a closed position over said archwire slot where said ligating slide member retains the orthodontic archwire therein and an open position clear of said archwire slot, said ligating slide member and said mounting base cooperatively having at least one resilient retention mechanism aligned in parallel relation to said ligating slide member and configured to resiliently deflect in a direction transverse to said path of travel and in a plane parallel with said ligating slide member to exert retaining forces in a plane parallel with said ligating slide member, thereby holding said ligating slide member in said closed position,
- wherein said ligating slide member is retained in said channel in both said closed and open positions and during movement therebetween.

53. The self ligating orthodontic bracket of claim 52, wherein said resilient retention mechanism comprises a pair of spaced resilient members defining a space and a projection received in said space and engaged by said resilient members which exert said retaining forces on said projection to retain said ligating slide member in said closed position.

54. The self ligating orthodontic bracket of claim 53, wherein said pair of spaced resilient members are carried by said ligating slide member and said projection is located on said base.

55. The self ligating orthodontic bracket of claim 53, wherein said pair of spaced resilient members and retaining forces are coplanar with said ligating slide member.

56. The self ligating orthodontic bracket of claim 52, wherein said ligating slide member includes an underside facing a bottom surface of said channel, one of said underside or bottom surface including a protruding stop and the other of said underside or bottom surface including a groove parallel with said path of travel, said stop being received in and moving along said groove during movement of the ligating slide member between said open and closed positions.

57. The self ligating orthodontic bracket of claim 56, wherein said groove and stop cooperate to limit movement of said ligating slide member along said path of travel in an opening direction.

58. The self ligating orthodontic bracket of claim 52, wherein said channel extends across said archwire slot and includes major and minor channel portions on opposite sides of said archwire slot.

59. The self ligating orthodontic bracket of claim 58, wherein said ligating slide member is retained in said major channel portion on one side of said archwire slot when said ligating slide member is in the open position and said ligating slide member includes a closure end configured to extend into said minor channel portion when said ligating slide member is in said closed position.

60. The self ligating orthodontic bracket of claim 59, wherein said resilient retention mechanism is arranged on said closure end and said minor channel portion.

61. The self ligating orthodontic bracket of claim 52, wherein said channel is defined between a pair of side walls parallel to said path of travel, an inside surface of each said side wall meeting a bottom surface of said channel to form a junction, each said inside surface extending from said junction to a top edge, said channel having a width between said inside surfaces that is greater at said junction than at said top edge.

62. The self ligating orthodontic bracket of claim 61, wherein said channel includes relief grooves formed at the junction of each side wall with said channel bottom surface.

* * * * *